United States Patent
Zhang et al.

(10) Patent No.: US 9,700,276 B2
(45) Date of Patent: Jul. 11, 2017

(54) ROBUST MULTI-OBJECT TRACKING USING SPARSE APPEARANCE REPRESENTATION AND ONLINE SPARSE APPEARANCE DICTIONARY UPDATE

(71) Applicants: Lei Zhang, Princeton, NJ (US); Wen Wu, East Windsor, NJ (US); Terrence Chen, Princeton, NJ (US); Norbert Strobel, Heroldsbach (DE); Dorin Comaniciu, Princeton Junction, NJ (US)

(72) Inventors: Lei Zhang, Princeton, NJ (US); Wen Wu, East Windsor, NJ (US); Terrence Chen, Princeton, NJ (US); Norbert Strobel, Heroldsbach (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 180 days.

(21) Appl. No.: 13/780,149

(22) Filed: Feb. 28, 2013

(65) Prior Publication Data
US 2013/0245429 A1 Sep. 19, 2013

Related U.S. Application Data

(60) Provisional application No. 61/604,000, filed on Feb. 28, 2012.

(51) Int. Cl.
| | |
|---|---|
| A61B 1/04 | (2006.01) |
| A61B 1/00 | (2006.01) |
| A61B 6/00 | (2006.01) |
| A61B 6/12 | (2006.01) |
| G06T 7/246 | (2017.01) |
| A61B 90/00 | (2016.01) |
| A61B 34/20 | (2016.01) |

(52) U.S. Cl.
CPC .............. *A61B 6/5211* (2013.01); *A61B 6/12* (2013.01); *A61B 6/485* (2013.01); *A61B 6/487* (2013.01); *G06T 7/248* (2017.01); *A61B 2034/2065* (2016.02); *A61B 2090/376* (2016.02); *G06T 2207/30021* (2013.01)

(58) Field of Classification Search
CPC .... A61B 2019/5238; A61B 2019/5265; A61B 6/12; A61B 6/485; A61B 6/487; A61B 6/5211; G06T 2207/30021; G06T 7/204
USPC ......... 600/424; 345/629–630, 634–635, 637, 345/639
See application file for complete search history.

(56) References Cited

U.S. PATENT DOCUMENTS

| | | | | |
|---|---|---|---|---|
| 5,267,328 | A * | 11/1993 | Gouge | 382/128 |
| 6,405,072 | B1 * | 6/2002 | Cosman | 600/426 |
| 6,484,049 | B1 * | 11/2002 | Seeley et al. | 600/426 |
| 6,567,949 | B2 * | 5/2003 | Heinen | G10L 19/005 704/230 |

(Continued)

*Primary Examiner* — John P Leubecker
*Assistant Examiner* — Arnaldo Torres Diaz

(57) ABSTRACT

A computer-implemented method for tracking one or more objects in a sequence of images includes generating a dictionary based on object locations in a first image included in the sequence of images. One or more object landmark candidates are identified in the sequence of images and a plurality of tracking hypothesis for the object landmark candidates are generated. A first tracking hypothesis is selected from the plurality of tracking hypothesis based on the dictionary.

19 Claims, 12 Drawing Sheets

(56) References Cited

U.S. PATENT DOCUMENTS

| | | | |
|---|---|---|---|
| 6,856,827 B2* | 2/2005 | Seeley et al. | 600/426 |
| 7,756,567 B2* | 7/2010 | Kuduvalli et al. | 600/427 |
| 7,844,320 B2* | 11/2010 | Shahidi | 600/424 |
| 7,920,732 B2* | 4/2011 | Shimizu et al. | 382/128 |
| 8,340,437 B2* | 12/2012 | Abramoff | G06K 9/6231 382/165 |
| 8,599,266 B2* | 12/2013 | Trivedi et al. | 348/169 |
| 8,649,606 B2* | 2/2014 | Zhao | G06K 9/4671 382/159 |
| 8,675,021 B2* | 3/2014 | Reusens et al. | 345/639 |
| 2006/0188139 A1* | 8/2006 | Khamene et al. | 382/130 |
| 2008/0025586 A1* | 1/2008 | Baumgart | A61B 6/06 382/128 |
| 2008/0051648 A1* | 2/2008 | Suri | A61B 6/481 600/407 |
| 2008/0219466 A1* | 9/2008 | Pishehvar | G10L 19/032 381/73.1 |
| 2010/0061597 A1* | 3/2010 | Kanda et al. | 382/107 |
| 2010/0183204 A1* | 7/2010 | Kanda | 382/128 |
| 2010/0220906 A1* | 9/2010 | Abramoff | G06K 9/6231 382/130 |
| 2011/0058026 A1* | 3/2011 | Kendrick | A61B 6/12 348/65 |
| 2011/0313285 A1* | 12/2011 | Fallavollita | A61B 6/4441 600/426 |
| 2012/0114215 A1* | 5/2012 | Baumgart | G06T 7/0012 382/132 |
| 2012/0230565 A1* | 9/2012 | Steinberg | G06T 7/0022 382/130 |
| 2013/0108131 A1* | 5/2013 | Abramoff | G06K 9/6231 382/131 |
| 2013/0113791 A1* | 5/2013 | Isaacs et al. | 345/419 |
| 2014/0051992 A1* | 2/2014 | Mostafavi | A61B 6/032 600/424 |
| 2014/0089000 A1* | 3/2014 | Takata et al. | 705/2 |
| 2014/0112566 A1* | 4/2014 | Steinberg | G06T 7/0022 382/131 |
| 2015/0018671 A1* | 1/2015 | Marentis | A61B 19/54 600/424 |
| 2015/0051480 A1* | 2/2015 | Hwang et al. | 600/424 |
| 2015/0164329 A1* | 6/2015 | Schmidt | A61B 5/0077 600/424 |
| 2015/0282890 A1* | 10/2015 | Cohen | A61B 6/5288 600/424 |

* cited by examiner

ROBUST MULTI-OBJECT TRACKING USING SPARSE APPEARANCE REPRESENTATION AND ONLINE SPARSE APPEARANCE DICTIONARY UPDATE

CROSS-REFERENCE TO RELATED APPLICATIONS

This application claims priority to U.S. provisional application Ser. No. 61/604,000 filed Feb. 28, 2012, which is incorporated herein by reference in its entirety.

TECHNOLOGY FIELD

The present invention relates generally to methods, systems, and apparatuses which utilize sparse appearance representation and online sparse appearance dictionary updating techniques for tracking objects presented in a sequence of images.

BACKGROUND

Atrial Fibrillation ("AF") is a rapid, highly irregular heartbeat caused by abnormalities in the electrical signals generated by the atria of the heart. AF is the most common cardiac arrhythmia and involves the two upper chambers of the heart. Surgical and catheter-based electrophysiology therapies have become common AF treatments throughout the world. Catheter ablation modifies the electrical pathways of the heart in order to treat the disease.

To measure electrical signals in the heart and assist the ablation operation, three catheters are inserted and guided to the left atrium. These three catheters include an ablation catheter, a circumferential mapping catheter, and a coronary sinus catheter. The operation is monitored with live fluoroscopic images for navigation guidance. Tracking three catheters with such different characteristics presents several challenges. Catheters have non-uniform appearance and shapes. In general, catheter characteristics include items such as tip electrode, size, spacing, and insertion length. Ablation catheters often have four electrodes with the tip electrode as a solid tube appearance in the fluoroscopic images, but may have electrode configuration different from each other. The circumferential mapping catheter has large intra-class variations because of differences in catheter diameter, electrode size, and number (i.e., number of poles and spacing). Coronary sinus catheters also vary from each other in terms of catheter length and electrode configuration. In addition, the three catheters may freely move within a large range and often occlude each other or other structures in the 2-D fluoroscopic images. During an electrophysiology operation such as an AF treatment, catheters may move into and out of an image. In addition, catheters are not rigid structures and may deform during the operation. Moreover, the use of fluoroscopic images presents additional challenges to tracking catheters in fluoroscopic images during the operation. Fluoroscopic images constantly change due to cardiac and respiratory motion and device movement. Additionally, structures in a fluoroscopic image often cause the background to be cluttered. The level of radiation may also affect the image quality and the signal to noise ratio.

SUMMARY

Embodiments of the present invention address and overcome one or more of the above shortcomings and drawbacks, by providing methods, systems, and apparatuses which utilize sparse appearance representation and online sparse appearance dictionary update techniques for tracking objects presented in a sequence of images. This technology is particularly well-suited for, but by no means limited to, tracking catheters in fluoroscopic images during AF ablation procedures and tracking objects in dynamic environments where the object appearance constantly changes due to change of the lighting conditions and/or shadows, for example. For the example of catheter tracking, using the techniques described herein, medical personnel may accurately track the location and motion of catheters in real-time during such procedures and this information may be stored in the system. In turn, the increased accuracy of such tracking may allow medical personnel to increase the effectiveness and minimize the risks of AF ablation procedures, as well as allow the medical personnel to review in-treatment catheter parameters such ablation locations, temperature, and force after the procedure is done.

Embodiments of the present invention are directed to a computer-implemented method for tracking one or more objects in a sequence of images. The method includes generating a dictionary based on object locations in a first image included in the sequence of images, identifying one or more object landmark candidates in the sequence of images, generating a plurality of tracking hypothesis for the object landmark candidates, and selecting a first tracking hypothesis from the plurality of tracking hypothesis based on the dictionary. In some embodiments, the sequence of images corresponds to a plurality of fluoroscopic images and at least some of the objects in the image correspond to at least one of a catheter tip and catheter electrode. In some embodiments, the first tracking hypothesis is selected from the plurality of tacking hypothesis by determining a confidence score for each tracking hypothesis and selecting the tracking hypothesis with the highest confidence score.

According to one aspect of the invention, foreground and background portions of the first image are determined. Then, a steerable filter or a pre-processing method is applied to the background portion to create a filtered image. The dictionary is then generated based on the filtered image. In other embodiments, the dictionary may be generated based on the background portion of the first image.

In some embodiments of the invention, a learning algorithm is applied to computed labels for each image in the sequence of images following a first image. Next, a plurality of images are selected based on the computed labels and used to update the dictionary. In one embodiment, the learning algorithm is a semi-supervised learning algorithm.

In another embodiment of the invention, one or more object landmark candidates in the sequence of images are identified by a two-step process. First, a first set of candidate samples included in the sequence of images is identified and a first stage probability score for each candidate samples in the first set is determined. Then, a second set of candidate samples from the first set is identified based on the first stage probability scores and a second stage probability score for each of the candidate samples in the second set is determined. The landmark candidates are then identified from the second set based on the second set probability scores.

According to one aspect of the invention, a first object landmark candidate corresponding to a first object type is identified using one or more first classifiers trained for the first object type and a second object landmark candidate corresponding to a second object type is identified using one or more second classifiers trained for the second object type. In some embodiments, the first object type corresponds to a catheter tip and the second object type corresponds to a catheter electrode. In some embodiments, each classifier is a probabilistic boosting tree.

According to another aspect of the invention, generating tracking hypothesis for object landmarks includes determining a set of landmarks in a previous image; calculating a plurality of translation vectors, each translation vector corresponding to a translation between one of the landmark candidates and one of the landmarks included in catheter model; generating a plurality of seed hypothesis by applying each of the translation vectors to the set of landmarks in the previous image; and applying a geometric transformation to each seed hypothesis to generate the plurality of tracking hypothesis. In some embodiments, the geometric transformation is an affine transformation.

Embodiments of the present invention are also directed to systems for tracking one or more objects in a sequence of images. The systems include a receiver module operably coupled to an imaging device and configured to receive a sequence of images from the imaging device. The system also include one or more first processors configured to generate a dictionary based on object locations in a first image included in the sequence of images and identify one or more object landmark candidates in the sequence of images. In some embodiments, these first processors are computational processor units (CPUs). The system also includes one or more second processors configured to generate a plurality of tracking hypothesis for the object landmark candidates and select a first tracking hypothesis from the plurality of tracking hypothesis based on the dictionary. In some embodiments, the second processors are graphical processing units.

Embodiments of the present invention are also directed at methods of updating a dictionary to represent change in appearance of a target object. First, the dictionary is generated based on an initial appearance of the target object in an initial image frame. Next, a plurality of subsequent image frames indicating a change in the initial appearance of the target object are received. Then a learning algorithm is used to compute labels for each of the subsequent image frames. A subset of the subsequent image frames are selected based on the computed labels. Finally, the dictionary is updated based on the subset of the subsequent image frames. In the some embodiments, the updated dictionary is then applied to track the target object in later image frames.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at the tracking multiple catheters during surgical procedures. However, one skilled in the art would recognize that the techniques described herein may also be applicable to other domains, allowing various types of objects to be tracked. Thus, the techniques described herein have applications both in surgical and non-surgical domains.

Figure 1:
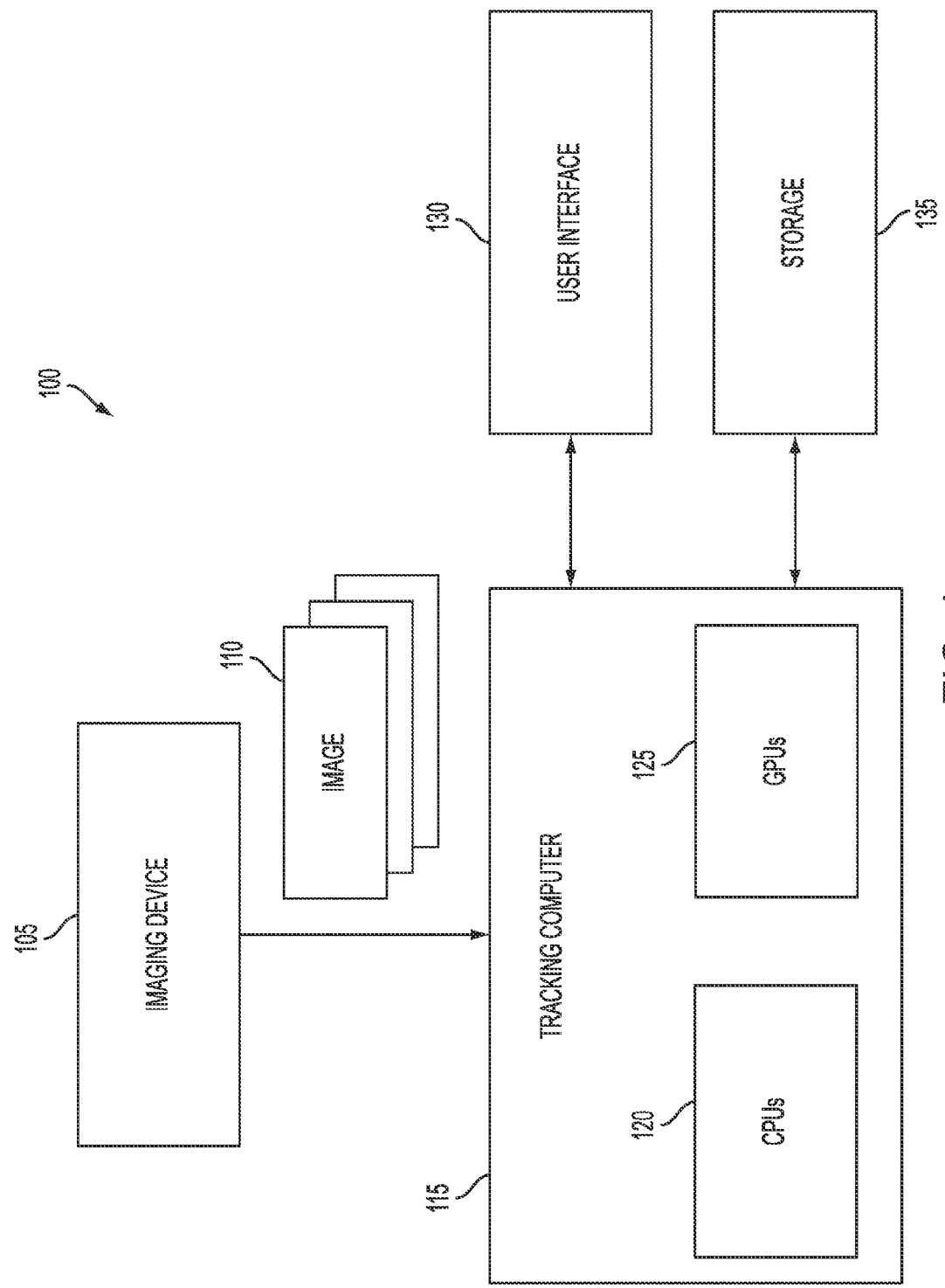
FIG. 1 is a perspective view of an object tracking system according to some embodiments of the present invention.

FIG. 1 is a perspective view of an object tracking system 100 according to some embodiments of the present invention. An imaging device 105 transfers one or more images 110 to a tracking computer 115. In one embodiment, the imaging device 105 is a C-Arm device (including an X-ray source and an image intensifier) and the images 110 are fluoroscopic images. In the example of FIG. 1, the tracking computer 115 includes one or more computational processing units (CPUs) 120 and one or more graphical processing units (GPUs) 125. As is well understood in the art, the use of CPUs in combination with GPUs provides various computation advantages in engineering applications, including a decreased latency in executing computationally intense algorithms. The imaging device 105 and the tracking computer 115 may be connected directly or indirectly using any technique known in the art. Thus, for example, in some embodiments the imaging device 105 and the tracking computer 115 are directly connected using a proprietary cable or an industry standard cable such as a Universal Serial Bus (USB) cable. In other embodiments, the imaging device 105 and the tracking computer 115 are indirectly connected over one or more networks (not shown in FIG. 1). These networks may be wired, wireless or a combination thereof.

Continuing with reference to FIG. 1, a user interface 130 is connected directly or indirectly to the tracking computer 115. The user interface 130 may include any interface known in the art including, for example and without limitation, a display, a keyboard, a mouse, and/or a touchscreen.

Storage 135 is also connected, either directly or indirectly, to the tracking computer 115. In some embodiments, the tracking computer 115 may communicate with the storage 135 to retrieve images (not shown in FIG. 1) as an alternative to receiving images 110 from the imaging device 105. Storage 135 may be implemented using any technique known in the art and may utilize, for example, any combination of magnetic, semi-conductor, and optical storage media.

Figure 2:
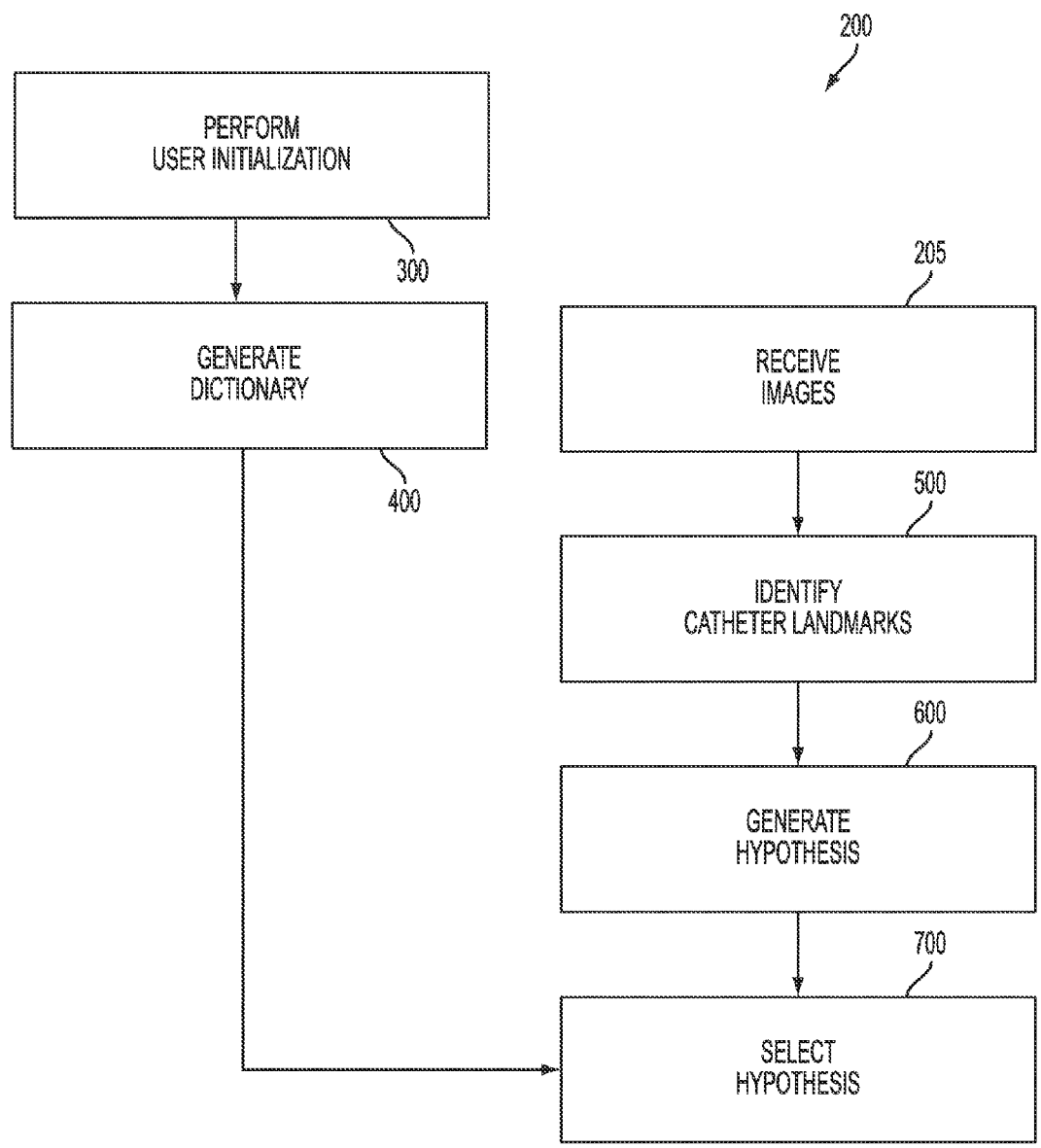
FIG. 2 is an illustration of a first object tracking framework according to one embodiment of the present invention.

FIG. 2 provides an illustration of a first object tracking framework 200 applicable to catheter tracking according to one embodiment of the present invention. At 300, a user initialization process identifies objects in one or more images. Next, at 400, a dictionary is learned to represent the structures of non-interest in fluoroscopic images. Such structures of non-interest may include, for example, catheter shafts and catheter wires appearing in a fluoroscopic image. Prior to, in parallel with, or after the dictionary is generated at 400, fluoroscopic images are received at 205 for tracking. At 500, catheter landmarks are identified in the received images. Next, at 600, one or more tracking hypothesis is generated based on the identified catheter landmarks. Then, at 700, a first tracking hypothesis is selected from the one or more tracking hypothesis based on the dictionary generated in 400.

Figure 3:
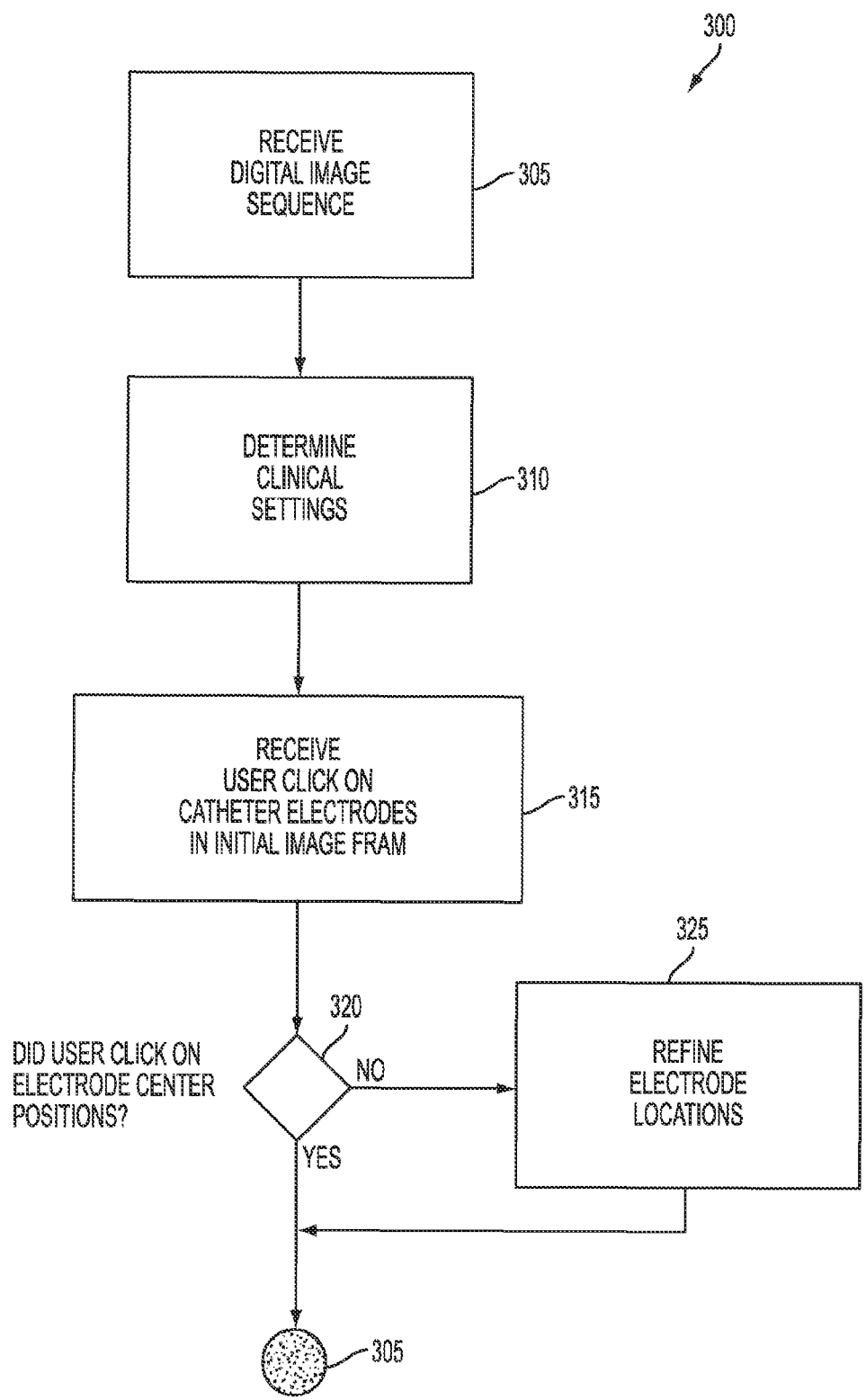
FIG. 3 illustrates a user initialization method according to one embodiment of the present invention.

FIG. 3 illustrates a user initialization process 300 according to one embodiment of the present invention, that may be used in the framework 200 shown in FIG. 2. At 305, a digital image sequence is received at the tracking computer 115, for example, via imaging device 105 (see FIG. 1). In some embodiments, where the imaging device 105 uses fluoroscopic imaging, the digital image sequence includes one or more fluoroscopic images. The digital imaging sequence may be received directly or indirectly through communication with the imaging device. Alternatively, the digital image sequence can be received by loading one or more digital images from storage 135. At 310, the tracking computer 115 determines one or more clinical settings. These clinical settings may include, for example, an X-ray dose level, C-arm angulation, and an indication of the presence of medical instruments. Some embodiments of the present invention only evaluate the clinical settings for an initial image in the digital image sequence. These embodiments assume that clinical settings will remain consistent during the rest of the procedure. Thus, dictionaries and other data items developed for an initial digital image may be utilized for representing subsequent digital images in the digital image sequence.

Continuing with reference to FIG. 3, at 315, a user clicks on catheter electrodes in an initial image digital image included in the digital image sequence, for example, via user interface 130. In some embodiments, the system requires the user to click on the catheter electrodes in a particular order, such as from the tip to the last electrode. At 320, the tracking computer 115 checks whether the user clicked on real electrode center positions. If the user did not click on real electrode center positions, the computer 115 refines the electrode locations at 325 to the center locations. In some embodiments, the locations of the center positions are refined automatically by the computer 115, while other embodiments require the user to provide additional input to the system. Finally, at 305, the process is finalized and the results are passed, for example, to a dictionary learning process such as illustrated in FIG. 4.

Figure 4:
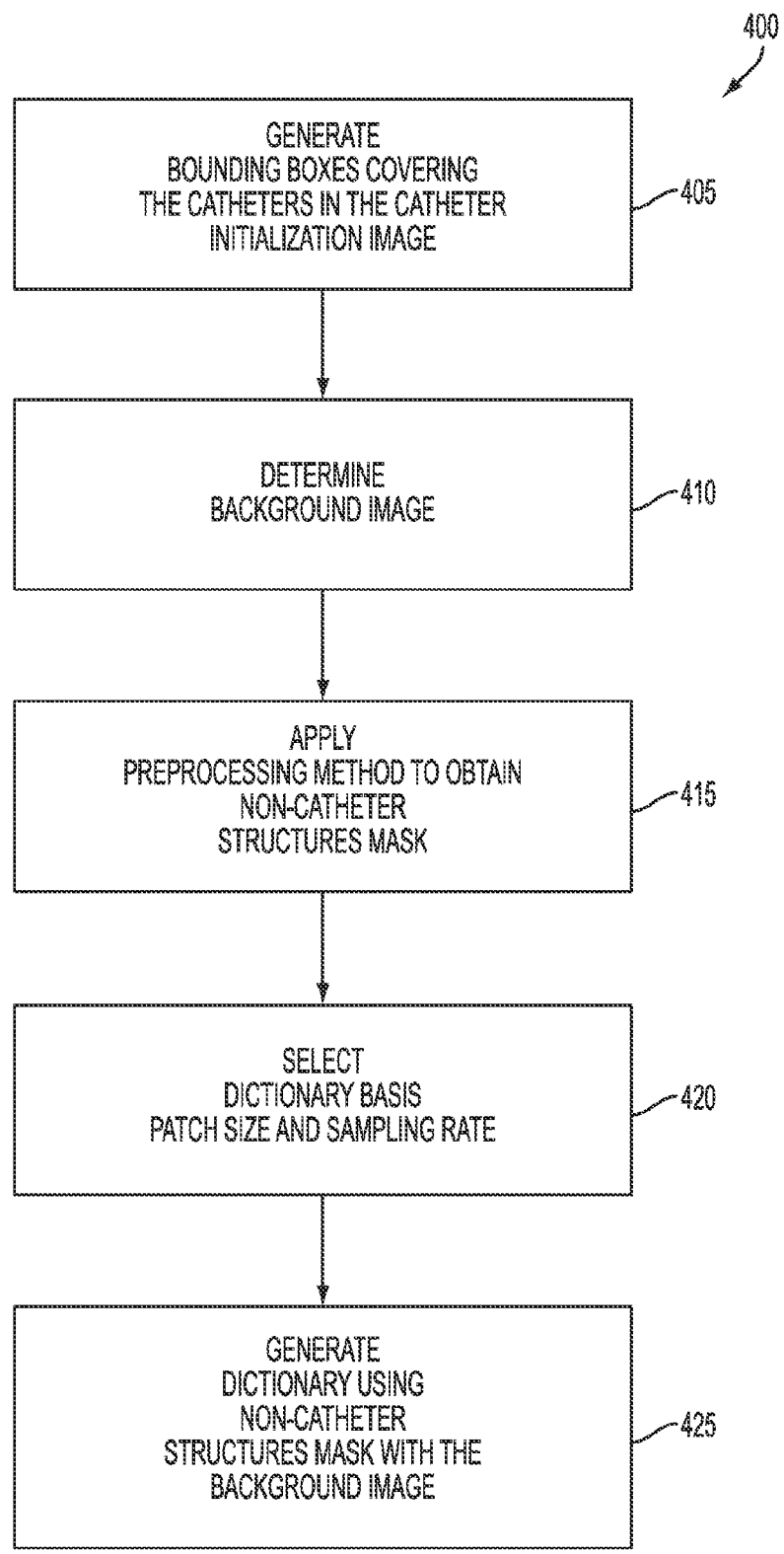
FIG. 4 illustrates a method for generating a dictionary for a sparse representation of structures or regions of non-interest in an image according to one embodiment of the present invention.

FIG. 4 provides a process 400 for generating a dictionary for a sparse representation of structures or regions of non-interest in an image according to one embodiment of the present invention. The process 400 begins at 405, where bounding boxes are generated for each catheter based on the catheter electrode locations. These boxes may be generated automatically or manually using any technique known in the art. For example in some embodiments, catheter electrode locations are identified (automatically or manually) and the boxes are automatically generated by drawing three-dimensional boxes of a predetermined area around each catheter electrode location. In other embodiments, the bounding boxes are generated manually by the user clicking and dragging a mouse pointer around a portion of the image surrounding a catheter electrode location. Once these bounding boxes have been generated, at 410, the background image is calculated by removing the portions of the image corresponding to the bounding box. Thus, the background image includes all portions of the original image with the exception of those portions corresponding to the catheters, as defined by the bounding boxes. Next, at 415, a pre-processing method is applied to the background image to obtain a non-catheters structures mask. In some embodiments, the pre-processing method is a steerable filter which detects ridge-like structures in the background image. As would be understood by one skilled in the art, ridge-like structures are sometimes falsely detected as catheter landmarks due to similar appearance and shape. The steerable filter may utilize image features including, without limitation, pixel intensity, to detect the ridge-like structures.

Continuing with reference to FIG. 4, at 420, a dictionary basis patch size and a sampling rate are selected. These values will be applied to partition the non-catheters structures mask to increase the computational efficiency of the learning the dictionary. For example, a 1024×1024 image may be down-sampled to 256×256 and partitioned into 7×7 image patches to minimize the computational processing required to learn the dictionary. Moreover, in some embodiments, the number of image patches is further reduced by assuming that the patches in the non-catheter structures mask are redundant in appearance. Thus, in these embodiments, the selection process of 420 may randomly sample a specified percentage of image pixels in the mask.

At 425, a dictionary $\Phi$ is generated using the non-catheter mask with the background image. In some embodiments, sparse coding is used to represent the non-catheter structures mask as several basis vectors in the dictionary. As would be understood by one skilled in the art, sparse coding allows a signal x to be represented as a linear combination of a one or more basis vectors in the dictionary $\Phi=[\phi_1 \ldots \phi_k]\in R^{n\times k}$. More generally, the signal may be represented by the equation:

$$x=\Phi\alpha+\epsilon,$$

where $\alpha$ are the coefficients of the bases and $\epsilon$ represents the noise. Given $\Phi$ and a dataset $X=\{x_i\}_{i=1}^N$, the solution of $\alpha$ may be formulated as a sparse coding product with the $l_0$ regularization:

$$\alpha^*=arg_\alpha \min \|\alpha\|_0, s.t. \Sigma_{i=1}^N \|x_i-\Phi\alpha_i\|^2 \leq \epsilon,$$

where $\|\cdot\|_0$ denotes the $l_0$-norm, which is the number on non-zero entries in the vector. Thus, given a dictionary $\Phi$ for each image patch x of an object, a sparse solution can be obtained by solving this optimization problem. However, the $l_0$ regularization presented above is non-convex and may be challenging to solve. Thus, in some embodiments, the $l_0$ regulation for $\alpha^*$ is reformulated as a convex optimization problem with the $l_1$ regulation:

$$\alpha^*=arg_\alpha \min \|\alpha\|_1, s.t. \Sigma_{i=1}^N \|x_i-\Phi\alpha_i\|^2 \leq \epsilon,$$

To learn the dictionary, an objective function is used. In some embodiments, where locality is more essential than sparsity, techniques such as Linear Locality Coding (LLC) may be used and the objective function may include one or more distance terms. For example, in some embodiments the objective function is defined as $$\Phi = arg_{\phi,\alpha} \Sigma_{i=1}^{N} \|x_i - \Sigma_{i=1}^{N}\|^2 + Q \|d_i \odot \alpha_i\|^2, s.t. \forall i, 1^T \alpha_i = 1,$$

where $\odot$ denotes element-wise multiplication and $d_i$ is the Euclidean distance vector between $x_i$ and the basis vectors in $\Phi$. To minimize the search required to find a solution for $\Phi$, methods such as K-selection may be used to perform basis selection.

In some embodiments, multiple dictionaries may be learned and used for object tracking. For example, the portions of the image corresponding to the objects are used to learn a positive dictionary, while the remaining portions (i.e., the background) may be used to learn a negative dictionary. Learning of the positive dictionary and negative dictionary may be performed simultaneously, in parallel, or sequentially.

Figure 5:
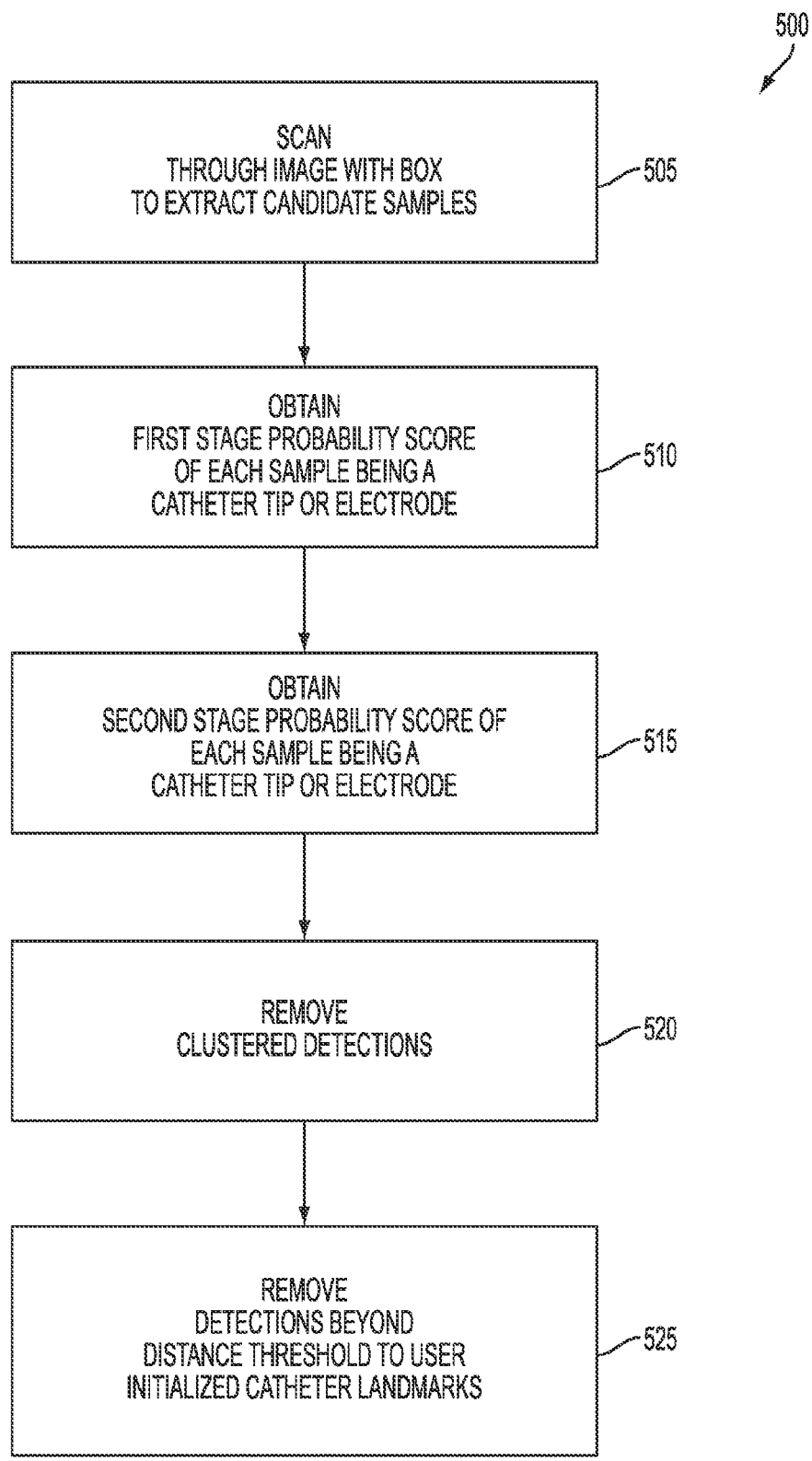
FIG. 5 is an example of a landmark identification process according to one embodiment of the present invention.

FIG. 5 is an example of a landmark identification process 500 that is performed prior to, in parallel with, or after building generation of the dictionary at 400. The process described in 500 is performed at the tracking computer 115 based on one or more images 110 received from the imaging device 105, or alternatively based on images retrieved from storage 135. In this process 500, discriminative models are learned based on catheter landmarks in an image including, without limitation, the catheter tip, electrodes, and body points. The catheter's tip and electrodes may be detected as oriented points (x, y, θ) parameterized by their position (x, y) and their orientation Θ. Information associated with landmark detection may be used throughout the object tracking framework 200, for example, to estimate catheter position, to prune the search space for catheter tracking, and to predict when catheters move into and out of images. Additional items may also be detected in the images to accurately bound the estimation of catheter motion and location. For example, in some embodiments, the collimator position on each side of the image is detected using a trained border detector based on Haar-like features.

As illustrated in the example of FIG. 5, at step 505, a box is used to scan through each image and extract candidate samples. The box-based representation is used to include both the tips, electrodes, and their respective context. Once the scan is complete, the candidates are processed by a two-stage detection process. This process utilizes two detectors that may be trained, for example, using a database of previously annotated images. At 510, a first stage detector processes each candidate sample to determine a first stage probability score for each candidate sample. The first stage detector is trained with target electrodes against randomly selected negative samples. Next, at 515, a second stage detector processes each candidate sample having a first stage probability score beyond a threshold value. The second stage detector is trained with the target electrodes against the false positives predicted by the first stage detector. Thus, the first stage is used to quickly remove negative candidate samples and the second stage is aimed at pruning out more confusing and/or difficult to process candidate samples. Following processing by the second stage detector at 515, a set of candidate samples are determined wherein each sample has a second stage probability score beyond a threshold value.

At 520, clustered detections are removed from the set of candidate samples to keep high-confident detections using a technique such as non-maximal suppression (NMS). In each image frame, a number of electrodes and tip candidates are selected and denoted as a catheter landmark candidate.

Then, at 525, any detection located greater than a threshold number of pixels from the initial catheter location (e.g., as identified by the process 300 illustrated in FIG. 3) is removed. Removal of these detections is based on the observation that during an ablation procedure, the catheters are moving inside the left atrium or coronary sinus and have limited range of motion. Thus, detections are not expected to move over a significant number of pixels between images.

Any detector known in the art may be used in the landmark detection process 500 illustrated in FIG. 5. In some embodiments, the detectors used in the landmark detection process 500 are based on Haar features. As would be understood by one skilled in the art, a Haar features-based detector is a tree-based structure which allows the posterior probability of the presence of the tip or electrodes may be calculated from the image data. The nodes in the tree are constructed by a non-linear combination of simple classifiers using boosting techniques. Thus, in these embodiments, a detector may provide a binary decision for a given sample, as well as a confidence value associated with the decision. Moreover, it should be noted that the tip of the catheter is different from other electrodes in terms of context and appearance. Thus, separate detectors may be trained for the tips and the electrodes.

For example, according to an embodiment of the present invention, each classifier is a Probabilistic Boosting Tree (PBT) that uses approximately 100,000 Haar features in a centered window of size $H_c \times H_c$. Classifiers in this embodiment output a probability $P(e=(x,y)|D)$. The detected candidate positions may then be augmented with a set of discrete orientations and fed to a trained oriented point detector. The oriented point detectors may use a richer feature pool including steerable feature responses and image intensity differences relative to the query position and orientation. Probabilistic Boosting Trees are described in greater detail in U.S. Pat. No. 7,702,596, issued Apr. 20, 2010, and entitled "Probabilistic Boosting Tree Framework for Learning Discriminative Models", which is incorporated herein by reference in its entirety.

To make the landmark detection process 500 more computationally efficient, techniques such as Marginal Space Learning ("MSL") may be used to first detect just the tip and electrode positions and then, at promising positions, search for all orientations. MSL is a fast object detection method that searches for objects in a sequence of increasing dimensions. Promising candidates from one subspace may be augmented with more parameters and a trained detector may be used to prune the new candidates. MSL is described in greater detail in U.S. Pat. No. 7,916,919, issued Mar. 29, 2011, and entitled "System and Method for Segmenting Chambers of a Heart in a Three Dimensional Image", which is incorporated herein by reference in its entirety.

Figure 6:
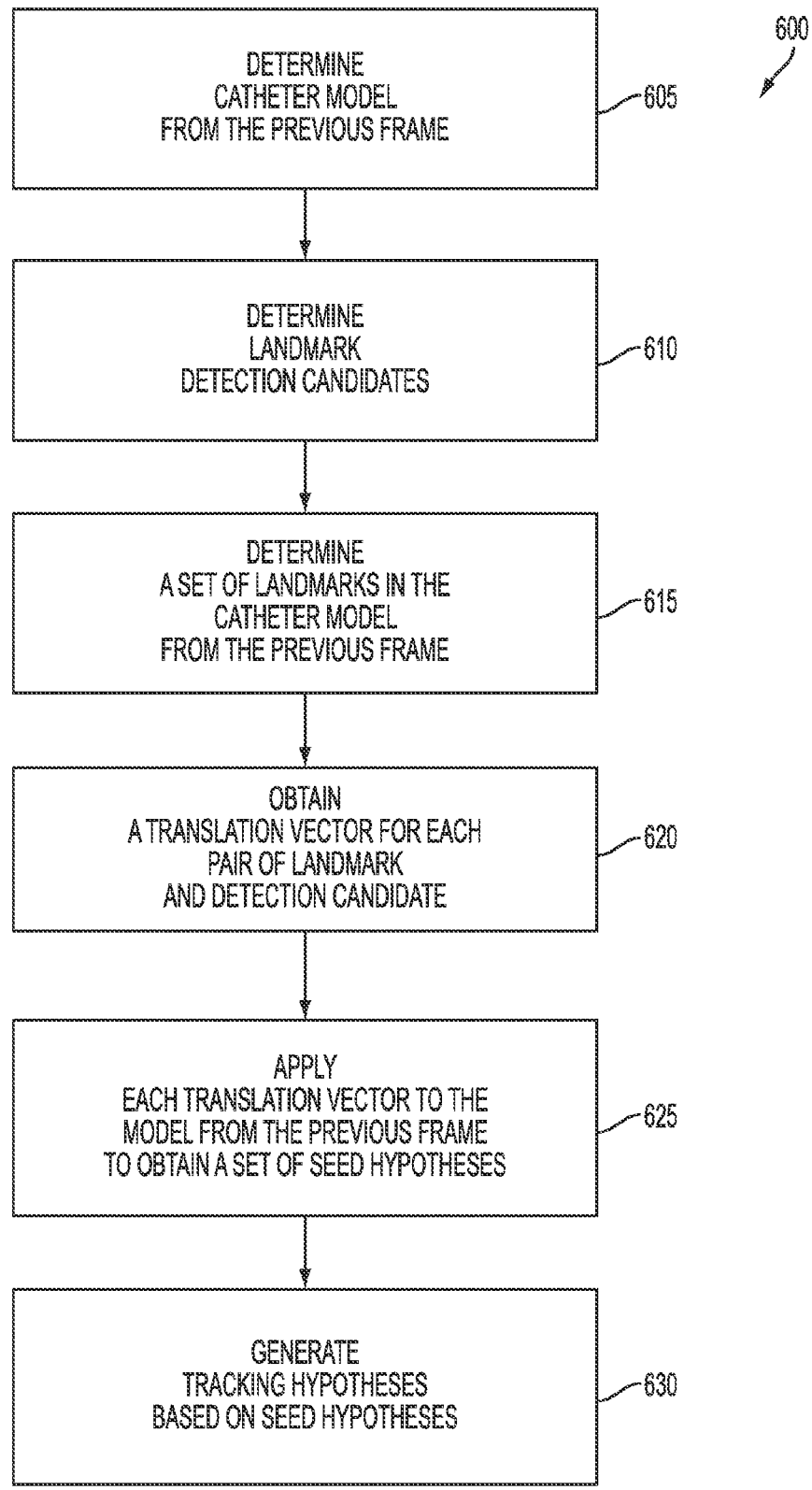
FIG. 6 illustrates an example of a process for generating model-based tracking hypotheses according to one embodiment of the present invention.

FIG. 6 provides an example process 600 for generating model-based tracking hypotheses according to one embodiment of the present invention. With catheter landmark detection locations identified by the landmark detection process 600, a model-based approach may be used to generate tracking hypotheses. The set of hypotheses is generated by parametrically manipulating the catheter model based on detected catheter tip and electrode candidates. The process 600 is a generalized framework that may be applied to all three catheters.

The example process 600 illustrated in FIG. 6 is initialized by first determining the catheter model $Y_{t-1} = \{e_{t-1}^1 \ldots e_{t-1}^L\}$ from the previous frame 605. Next, at 610, the landmark detection candidates $\{L_t^x\}$ output from the landmark detection process 500 (see FIG. 5) are determined.

Following initialization, the set of landmarks $\{Y_{t-1}^r\}$ in the catheter model from the previous frame are determined at 615. Next, at 620, for each pair of one landmark and one detection candidate ($\{Y_{t-1}^r\}$ and $L_t^{Yj}$), a translation vector $S_{rj}$ is computed from the landmark to the detection candidate. Thus, a set of translation vectors is obtained at 615. Then, at 625 a set of seed hypotheses are generated by applying each $S_{rj}$ to $Y_{t-1}$. Finally, at 630, the translated landmark in the seed hypothesis is considered to be a transformation center and a set of mathematical transformations is applied to generate tracking hypothesis $\{Y_t^\alpha\}$. For example, in some embodiments, affine transformations of the landmarks may be obtained by sampling transformation parameters within a predetermined range to generate the tracking hypothesis.

Figure 7:
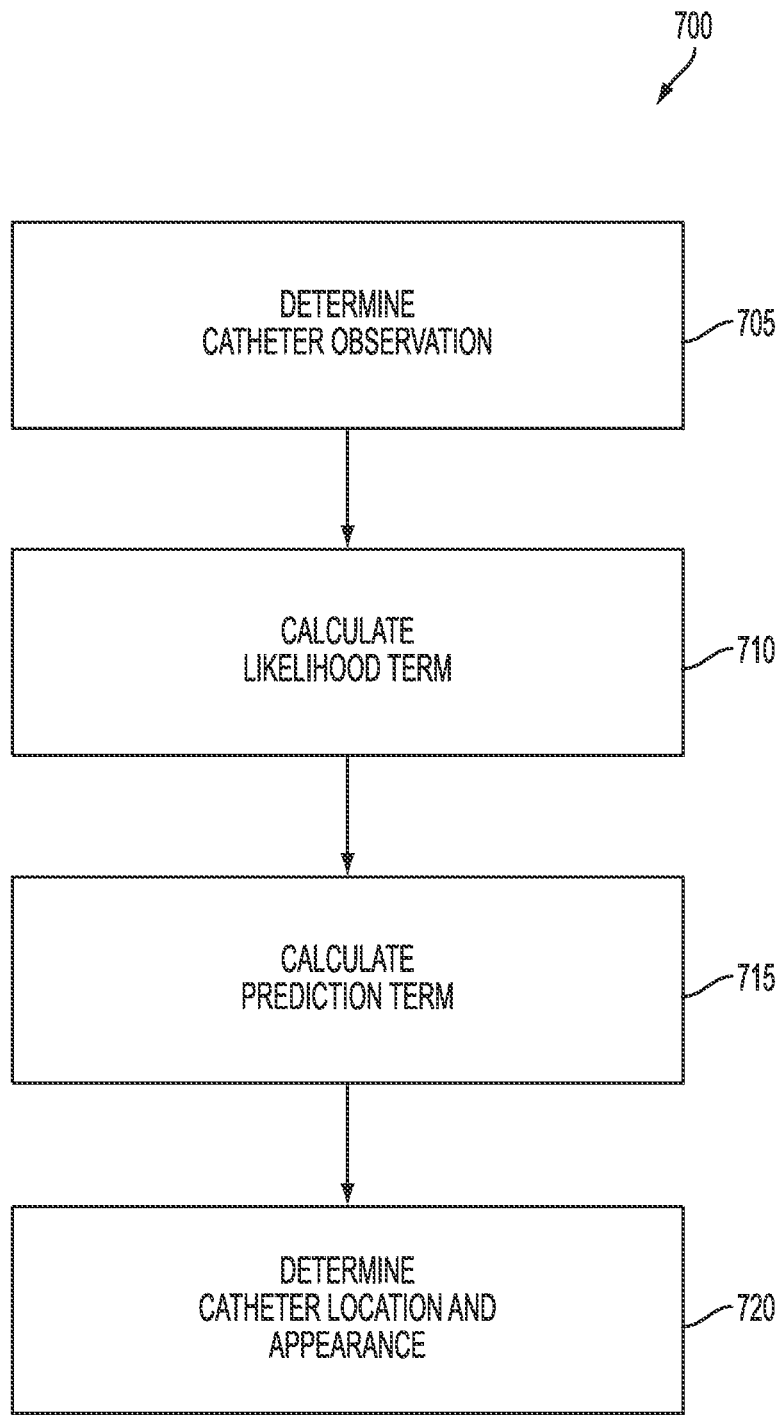
FIG. 7 illustrates an example of an adaptive process for evaluating a tracking hypothesis according to one embodiment of the present invention.

FIG. 7 is an example of an adaptive process 700 for evaluating the tracking hypothesis generated in 600 according to one embodiment of the present invention. In the example of FIG. 7, tracking hypotheses are evaluated according to a Bayesian inference framework which assumes a Markovian model of catheter motion. From catheter observation $Z_{0\ldots t}$, the catheter's state (i.e., location and appearance) $Y^*_t$ may be determined by a Maximum A Posteriori (MAP) estimation:

$$Y^*_t = arg_\alpha max P(Y_t^\alpha | Z_{0\ldots t})$$

Markovian representation of catheter motion leads to:

$$Y^*_t = arg_{Y_t^\alpha} max P(Z_t|Y_t^\alpha) P(Y_t^\alpha | Y^*_{t-1}) P(Y^*_{t-1} | Z_{0\ldots t-1})$$

The formula for $Y^*_t$ combines two parts: a likelihood term, $P(Z_t|Y_t^\alpha)$ and a prediction term $P(Y_t^\alpha | Y^*_{t-1})$.

Continuing with reference to FIG. 7, at 705 the catheter observation is determined. Then, at 710, the likelihood term (also referred to as "a confidence score") is calculated based on this observation. In some embodiments, $P(Z_t|Y_t^\alpha)$ is estimated by combining landmark detection probability, scene representation, and catheter body template matching via an occlusion reasoning framework:

$$P(Z_t|Y_t^\alpha) = (1-\lambda \cdot \delta_o) \cdot P(L^*_t|Y_t^\alpha) P(\overline{B}^*_t|Y_t^\alpha) + \lambda \cdot \delta_o \cdot P(T_{t-1}^Y|Y_t^\alpha),$$

where $P(L^*_t|Y_t^\alpha)$ is the estimated detection probability measure about catheter landmarks at the t—the frame that assists estimation of $Y_t$. $T_{t-1}^Y$ is the template for the catheter Y, while $\lambda$ is a weight factor computed by the normalized cross-correlation ("NCC") score. The $P(\overline{B}^*_t|Y_t^\alpha)$ term indicates the probability that the hypothesized model is not a part of the scene. This probability may be computed using a dictionary $\Phi$ (e.g., learned by the process 400 described in FIG. 4):

$$P(\overline{B}^*_t|Y_t^\alpha) = 1 - \prod_{x_i \in Y_t^\alpha} e^{-\frac{\|x_i - \Phi \alpha_i\|^2}{\sigma^2}}$$

Some embodiments of the present invention include an occlusion factor $\delta_O$ in the calculation of the likelihood term at 710. In AF ablation fluoroscopic images, catheters freely move inside the heart chamber and often occlude with each other or other structures. When occlusion occurs, integration of intensity-based normalized cross-correlation ("NCC") matching in the MAP estimation may introduce noise. Therefore, the framework described herein may reason an occlusion map using the scene sparse representation and catheter landmark detection candidates. Assume two or more objects occlude each other in the image, and denote the interacting region as $S_t$; the goal is to assign a label, $o_i$, from the set {occlusion as 1, no occlusion as 0} to each pixel, $x_i$, in $S_t$ to obtain a label set $O_t$. The occlusion factor $\delta_O$ in the equation for $P(Z_t|Y_t^\alpha)$ may be computed as $$O_t(x_i) = \begin{cases} 0 & \text{if } \sum_{x_i \in Y_t^\alpha} O_t(x_i) \geq v\|Y_t^\alpha\| \\ 1 & \text{if } \sum_{x_i \in Y_t^\alpha} O_t(x_i) < v\|Y_t^\alpha\| \end{cases}$$

where v is the occlusion threshold and $\|Y_t^\alpha\|$ is the model size. The occlusion inference is using the catheter landmark detection probability maps and fluoroscopic scene probability map. The methods described herein may be used to track all three catheters used for atrial fibrillation ablation procedures. Therefore, four maps are used to compute $O_t(x_i)$. More specifically, $O_t(x_i)$ may be defined as:

$$O_t(x_i) = \begin{cases} 1 & \text{if } \exists (k, l) P_t^k(x_i) > \tau \text{ and } P_t^l(x_i) > \tau \\ 0 & \text{if otherwise} \end{cases}$$

where $P_t^k$ represents each probability map. Using the scene representation and landmark detection probability, the likelihood term is dynamically estimated via occlusion reasoning. The catheter landmark detectors are trained using a large amount of data covering various object-context scenarios including occlusion and catheter foreshortening. As one skilled in the art would understand, occlusion reasoning integrates NCC matching score for non-occlusion hypothesis evaluation and utilizes the landmark detection probability and scene sparse representation in case of occlusion.

Returning to FIG. 7, at 715, the prediction term $P(Y_t^\alpha | Y^*_{t-1})$ in the equation for $Y^*_t$ is calculated. In some embodiments, the prediction term may be modeled as a Gaussian mixture model:

$$P(Y_t^\alpha | Y^*_{t-1}) = \sum_{k=0}^{M} p_k \cdot g_k(Y_t, u_k, \sigma_k),$$

where $g_0(\cdot)$ is updated by the tracking result of the previous frame $Y_{t-1}$. The values for $g_0(\cdot) \forall k, k \neq 0$ are learned from the training database to represent the most probable catheter locations in the fluoroscopic image. Finally, at 720, the likelihood term and the prediction term are used to calculate the catheter's location and appearance $Y^*_t$.

In some embodiments of the present invention a voting map comprised of image patches is used to localize the target location. For each landmark candidate, a voting score is calculated by considering the voting contribution of each of the patches. The image patch with the largest voting score is then used to select the targets and may also be used to update the dictionary.

Since the model-based hypotheses are generated in a discrete space, small location errors may be present even with the best candidate. In order to refine the results, in some embodiments of the invention, the tracking estimation is refined by searching for a local maximum in the parameter space. Any search technique known in the art may be used to perform the searching including, for example, Powell's conjugate gradient descent.

Foreground and background structures in a fluoroscopic image sequence change and move from image to image. Using the template learned at catheter initialization 400 may not be sufficient to overcome the catheter appearance change due to device movement and heart motion. Thus, in some embodiments, the catheter template is dynamically updated and to MAP estimation of $Y^*_t$. The catheter model may be updated online as:

$$T_t^Y = (1-\phi^Y) \cdot T_{t-1}^Y + \phi^Y \cdot l(Y^*_t),$$

where $T_t^Y$ represents the catheter template and $l(Y^*_t)$ is the image patch of $Y^*_t$. Thus, the high-confidence localized catheter appearance in the current image may be fused with the learned template.

Figure 8:
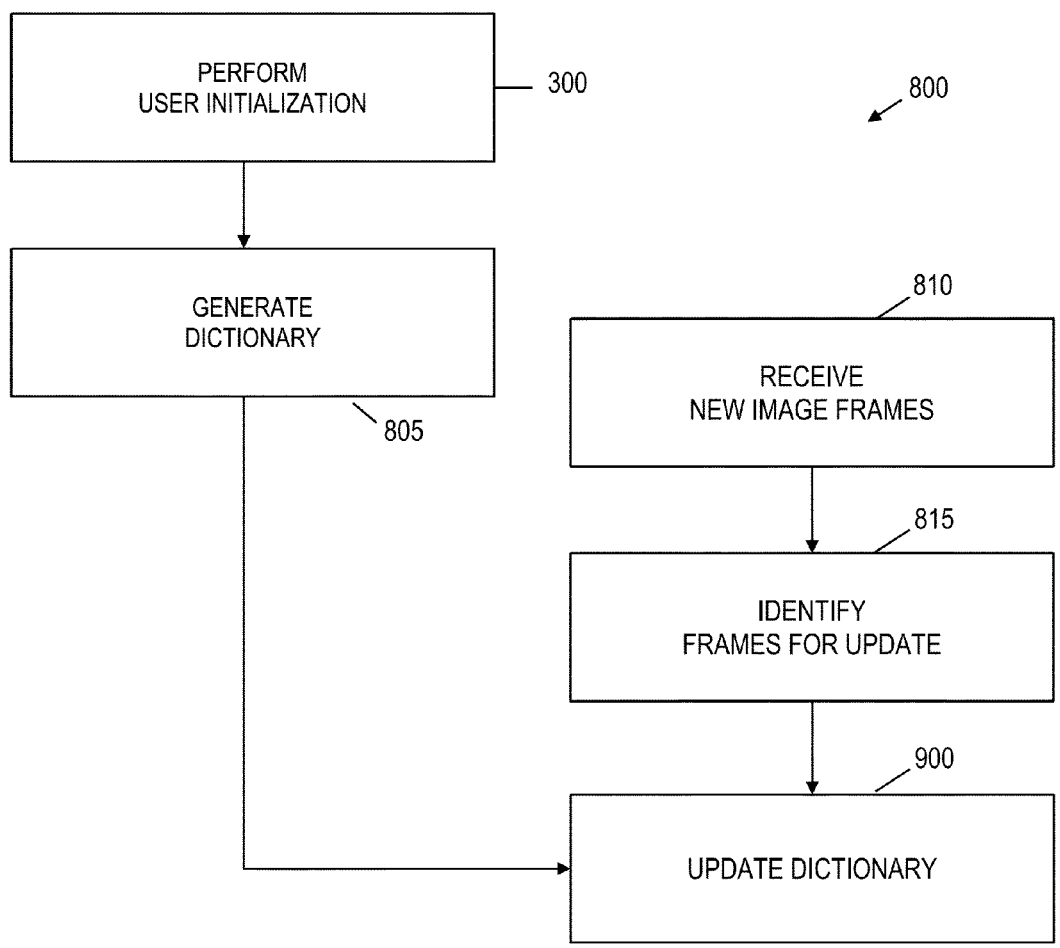
FIG. 8 is an illustration of a second object tracking framework according to one embodiment of the present invention.

FIG. 8 provides an illustration of a second object tracking framework 800 according to one embodiment of the present invention. The framework 800 applies a semi-supervised learning-based dictionary update to handle changes and variations in an object's appearance across a sequence of image frames. This framework 800 may be applied to various object tracking scenarios including, but not limited to, catheter tracking. At 300, a user initialization process identifies object locations in an image frame. It should be noted that although the framework 800 illustrated in FIG. 8 utilizes the user initialization process 300 illustrated in FIG. 3, other user initialization processes may also be used with the framework 800. The object locations provided by the user during the initialization process 300 are used at 805 to learn a dictionary which includes a sparse representation of the object's initial appearance in the image frame. This dictionary may be learned using any technique known in the art.

Continuing with reference to FIG. 8, at 810, new image frames are received, for example via imaging device 105 (see FIG. 1), showing a change in the appearance of the objects over time. Rather than performing a dictionary update for each new image frame received, at 815 the framework 800 identifies image frames for performing an update based on feature analysis of each frame. In some embodiments, a classifier trained based on manually labeled frames is used to identify new image frames for performing the dictionary update. The training data used in such a classifier may include one or more video sequences, each having one or more image frames. Each video sequence and/or image frame included in the training data may be labeled as either "update" or "non-update" based on the features presented therein. Any features known in the art may be used to identify image frames for updating. In some embodiments, these features include, without limitation, a template matching score, a sparse appearance modeling confidence, and histogram matching score. Temporal features may also be used. Thus, temporal features may be computed from two frames with P-frame interval and other statistics such as the mean and variance of a particular feature may be computed over the past K frames. The values of P and K are parameters that may be adjusted when generating the temporal features. Finally, at 900, the dictionary is updated with the new appearance information of the object found in the identified frames by applying one or more semi-supervised learning algorithms.

Figure 9:
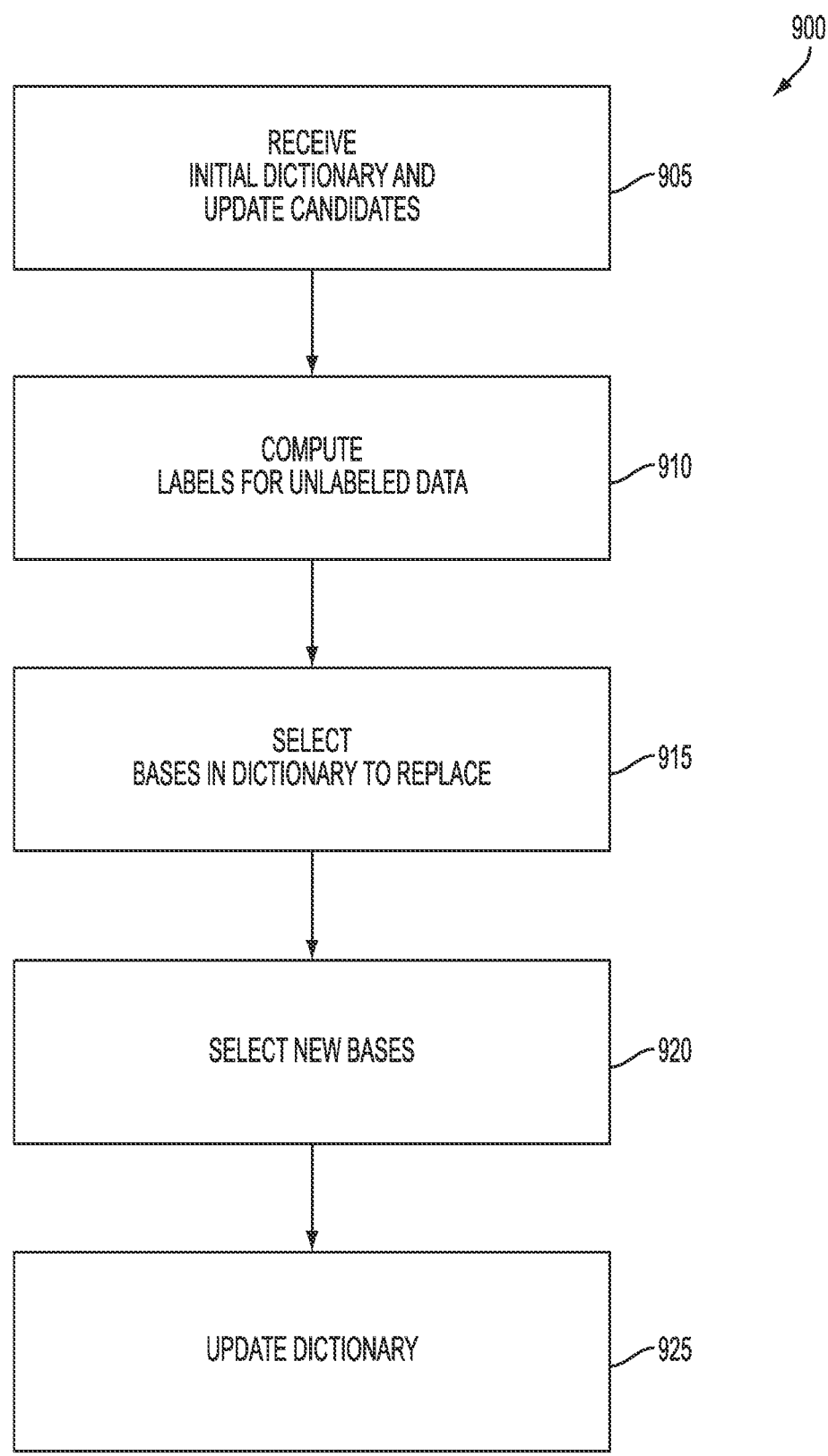
FIG. 9 illustrates a semi-supervised learning-based online dictionary update process according to one embodiment of the present invention.

FIG. 9 illustrates a semi-supervised learning-based online dictionary update process 900 that may be used, for example, in the framework 800 illustrated in FIG. 8. At 905, an initial dictionary $\Phi$ is received along with a set of new image frames. These new image frames, referred to herein as "dictionary update candidates" may be identified, for example, according to the process described above with respect to 815 (see FIG. 8). Next, at 910, a learning algorithm is applied to compute labels for the update candidates. In one embodiment, a semi-supervised learning ("SSL") algorithm is used. As understood by one skilled in the art, an SSL algorithm is a machine learning technique which utilizes both labeled and unlabeled data for training examples. Thus, in the example of FIG. 9, the training examples may include existing dictionary elements as labeled data and the update candidates as unlabeled data. The SSL algorithm is then used to compute the labels for the unlabeled data (i.e., the update candidates).

Continuing with reference to FIG. 9, at 915, the dictionary data is sorted, in ascending order, by how frequently each item in the dictionary is used. This sorting identifies bases in the dictionary which are not frequently used and, thus, may be replaced by new bases from the candidate data. Then, at 920, the candidate data is sorted in an ascending order based on the labels provided by the learning algorithm. Finally, at 925, the dictionary is updated based on the sorted dictionary and candidate data. In one embodiment, the dictionary is updated according to the following equation:

$$\Phi_{new} = (\Phi \backslash P_r) \cup U_r,$$

where $P_r$ and $U_r$ represent the first r basis in the sorted basis of the dictionary and candidate data, respectively.

Figure 10:
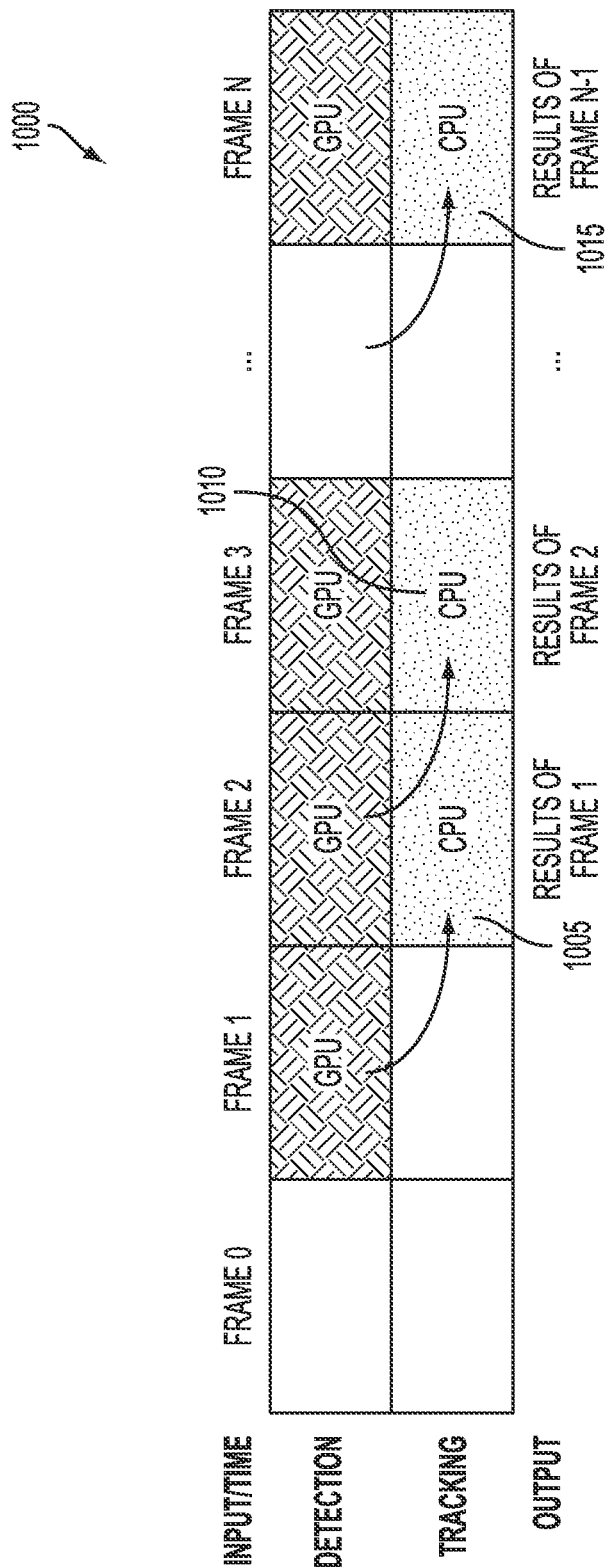
FIG. 10 illustrates a CPU-GPU computation framework, according to some embodiments of the present invention.

As demonstrated in the example of FIG. 1, the object tracking system 100, the tracking computer 115 may include both CPUs 120 and GPUs 125. In many embodiments of the present invention, the object tracking system 100 operates in real-time or near real-time. Thus, at each time interval (dependent on the fluoroscopy frame rate) the system 100 may receive one or more new fluoroscopic images. While receiving images at this rate, it may be challenging to fully take advantage of a GPUs many-core computation capability because of lack-of-large-amount-of-data. FIG. 10 illustrates a CPU-GPU computation framework 1000 where catheter landmark detection is performed by GPUs and tracking computation is performed by CPUs. In FIG. 10, the arrows 1005, 1010, and 1015 depict the data flow between frames. For example, at the n-th frame, the framework 1000 may assign a GPU to perform catheter tip and electrode detection, while a CPU performs catheter electrode tracking using the detection results of the (n−1)-th frame. By doing this, the framework 1000 maximizes use of both the CPU and the GPU resources computation. Although this approach may delay the output of tracking results by one-frame interval, this time is usually acceptable in clinical settings and can be further reduced at higher fluoroscopic acquisition frame rate.

Figure 11:
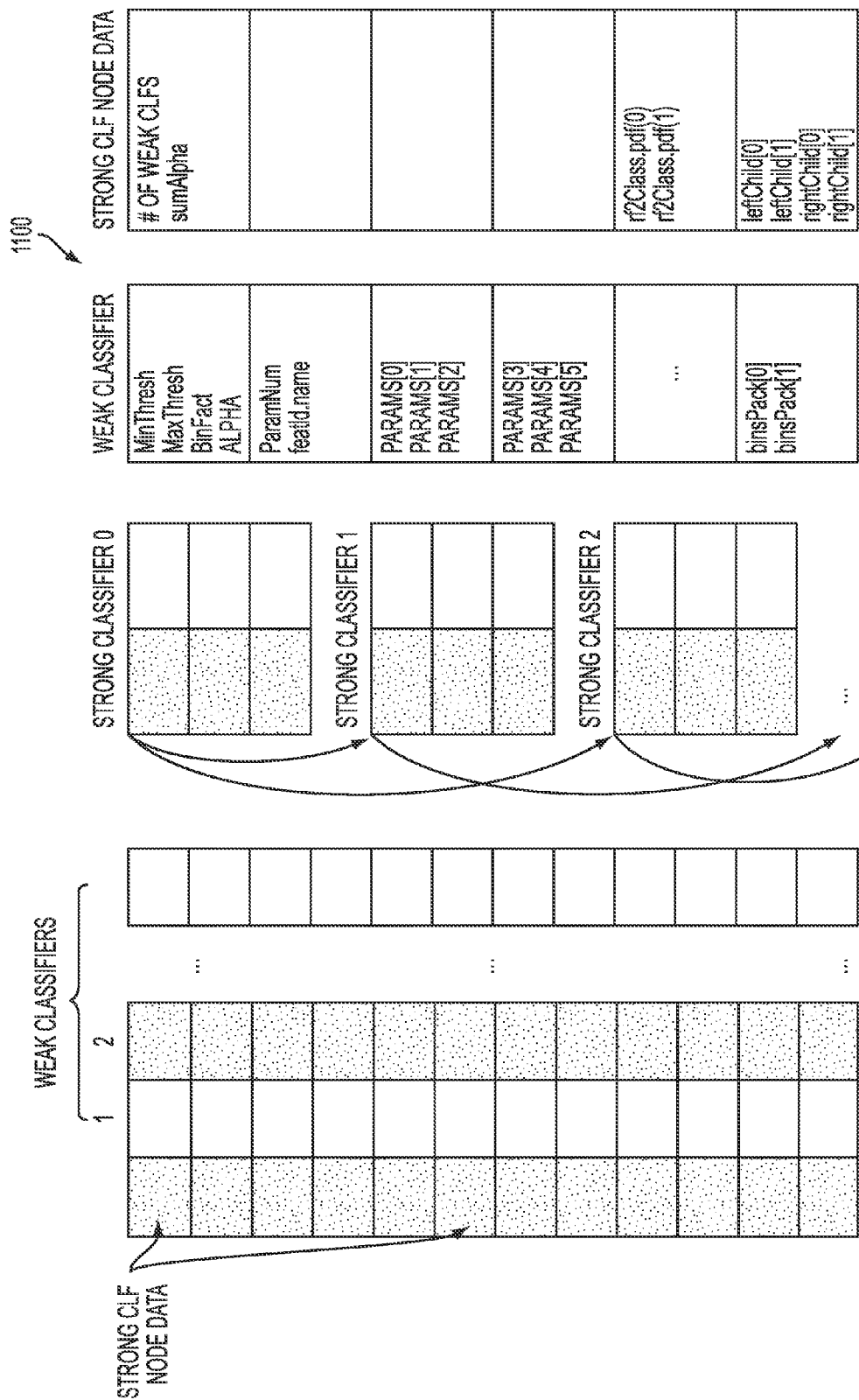
FIG. 11 illustrates an example implementation of a probabilistic boosting-tree classifier in GPU texture memory, according to some embodiments of the present invention.

FIG. 11 illustrates the implementation of the probabilistic boosting-tree (PBT) classifier in GPU texture memory 1100, which include the strong classifier node data and the weak classifier data, according to some embodiments of the present invention. During detection, the PBT kernel is launched and executed on the GPU device by many thousands of threads, each of which takes one candidate image position as input. The GPU texture memory spaces reside in GPU device memory and are cached in texture cache, so a texture fetch or surface read costs one memory read from device memory only on a cache miss, otherwise it just costs one read from texture cache. The texture cache is optimized for 2D spatial locality, so threads of the same warp that read texture or surface addresses that are close together in 2D will achieve the best performance. Reading device memory through texture thus becomes an advantageous alternative to reading device memory from global or constant memory.

Figure 12:
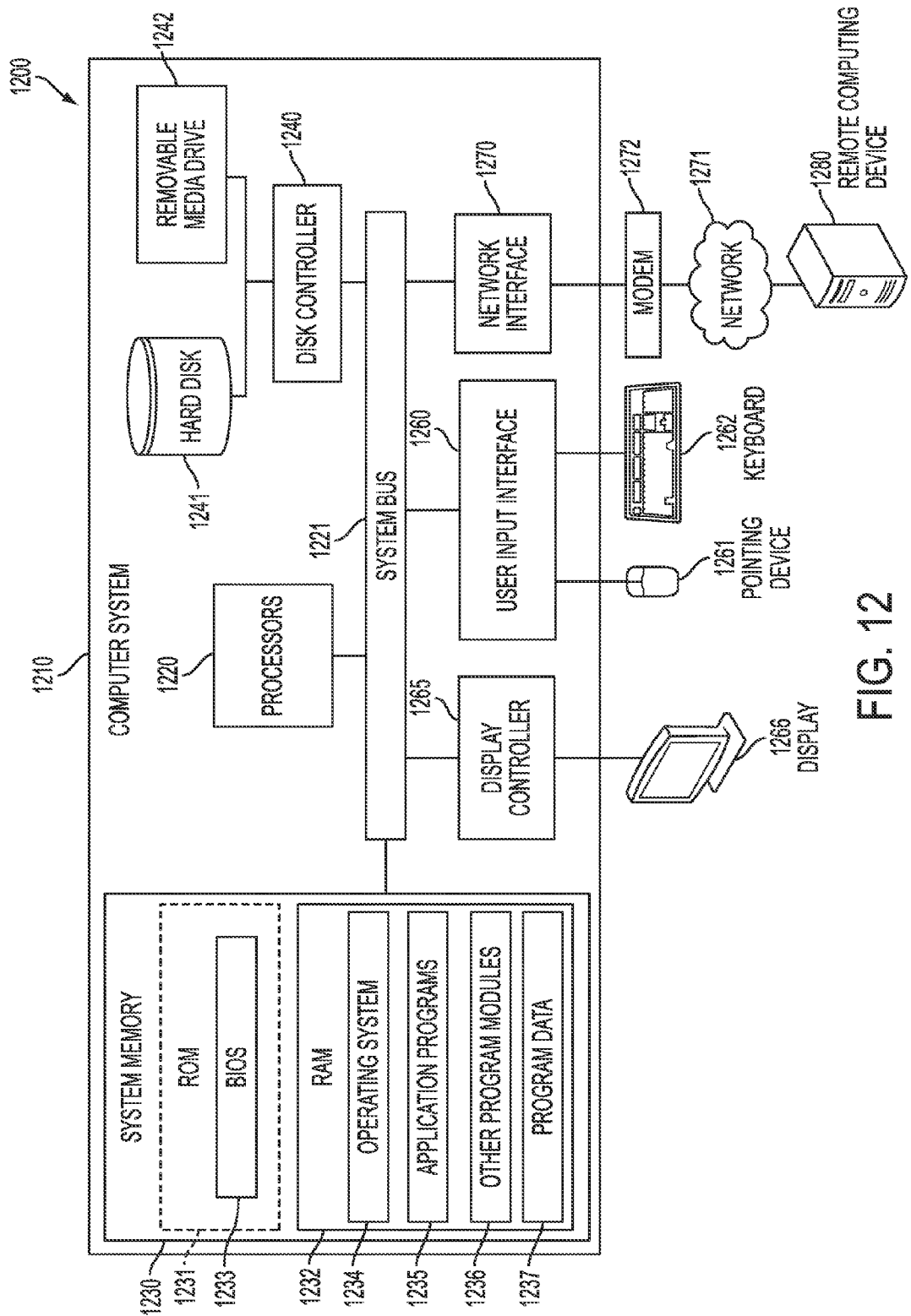
FIG. 12 illustrates an example of a computing environment within which embodiments of the invention may be implemented.

FIG. 12 illustrates an example of a computing environment 1200 within which embodiments of the invention may be implemented. Computing environment 100 may include computer system 1210, which is one example of a general purpose computing system upon which embodiments of the invention may be implemented. Computers and computing environments, such as computer 1210 and computing environment 1200, are known to those of skill in the art and thus are described briefly here.

As shown in FIG. 12, the computer system 1210 may include a communication mechanism such as a bus 1221 or other communication mechanism for communicating information within the computer system 1210. The system 1210 further includes one or more processors 1220 coupled with the bus 1221 for processing the information. The processors 1220 may include one or more central processing units (CPUs), graphical processing units (GPUs), or any other processor known in the art.

The computer system 1210 also includes a system memory 1230 coupled to the bus 1221 for storing information and instructions to be executed by processors 1220. The system memory 1230 may include computer readable storage media in the form of volatile and/or nonvolatile memory, such as read only memory (ROM) 1231 and/or random access memory (RAM) 1232. The system memory RAM 1232 may include other dynamic storage device(s) (e.g., dynamic RAM, static RAM, and synchronous DRAM). The system memory ROM 1231 may include other static storage device(s) (e.g., programmable ROM, erasable PROM, and electrically erasable PROM). In addition, the system memory 1230 may be used for storing temporary variables or other intermediate information during the execution of instructions by the processors 1220. A basic input/output system (233 (BIOS) containing the basic routines that help to transfer information between elements within computer system 1210, such as during start-up, may be stored in ROM 1231. RAM 1232 may contain data and/or program modules that are immediately accessible to and/or presently being operated on by the processors 1220. System memory 1230 may additionally include, for example, operating system 1234, application programs 1235, other program modules 1236 and program data 1237.

The computer system 1210 also includes a disk controller 1240 coupled to the bus 1221 to control one or more storage devices for storing information and instructions, such as a magnetic hard disk 1241 and a removable media drive 1242 (e.g., floppy disk drive, compact disc drive, tape drive, and/or solid state drive). The storage devices may be added to the computer system 1210 using an appropriate device interface (e.g., a small computer system interface (SCSI), integrated device electronics (IDE), Universal Serial Bus (USB), or FireWire).

The computer system 1210 may also include a display controller 1265 coupled to the bus 1221 to control a display or monitor 1265, such as a cathode ray tube (CRT) or liquid crystal display (LCD), for displaying information to a computer user. The computer system includes an input interface 1260 and one or more input devices, such as a keyboard 1262 and a pointing device 1261, for interacting with a computer user and providing information to the processor 1220. The pointing device 1261, for example, may be a mouse, a trackball, or a pointing stick for communicating direction information and command selections to the processor 1220 and for controlling cursor movement on the display 1266. The display 1266 may provide a touch screen interface which allows input to supplement or replace the communication of direction information and command selections by the pointing device 1261.

The computer system 1210 may perform a portion or all of the processing steps of embodiments of the invention in response to the processors 1220 executing one or more sequences of one or more instructions contained in a memory, such as the system memory 1230. Such instructions may be read into the system memory 1230 from another computer readable medium, such as a hard disk 1241 or a removable media drive 1242. The hard disk 1241 may contain one or more datastores and data files used by embodiments of the present invention. Datastore contents and data files may be encrypted to improve security. The processors 1220 may also be employed in a multi-processing arrangement to execute the one or more sequences of instructions contained in system memory 1230. In alternative embodiments, hard-wired circuitry may be used in place of or in combination with software instructions. Thus, embodiments are not limited to any specific combination of hardware circuitry and software.

As stated above, the computer system 1210 may include at least one computer readable medium or memory for holding instructions programmed according embodiments of the invention and for containing data structures, tables, records, or other data described herein. The term "computer readable medium" as used herein refers to any medium that participates in providing instructions to the processor 1220 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1241 or removable media drive 1242. Non-limiting examples of volatile media include dynamic memory, such as system memory 1230. Non-limiting examples of transmission media include coaxial cables, copper wire, and fiber optics, including the wires that make up the bus 1221. Transmission media may also take the form of acoustic or light waves, such as those generated during radio wave and infrared data communications.

The computing environment 1200 may further include the computer system 1220 operating in a networked environment using logical connections to one or more remote computers, such as remote computer 1280. Remote computer 1280 may be a personal computer (laptop or desktop), a mobile device, a server, a router, a network PC, a peer device or other common network node, and typically includes many or all of the elements described above relative to computer 1210. When used in a networking environment, computer 1210 may include modem 1272 for establishing communications over a network 1271, such as the Internet. Modem 1272 may be connected to system bus 1221 via user network interface 1270, or via another appropriate mechanism.

Network 1271 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1210 and other computers (e.g., remote computing system 1280). The network 1271 may be wired, wireless or a combination thereof. Wired connections may be implemented using Ethernet, Universal Serial Bus (USB), RJ-12 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1271.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A computer-implemented method for tracking one or more catheter objects in a sequence of images, the method comprising:
    determining, by a computer, a foreground portion of the first image comprising portions of the first image corresponding to one or more catheter electrode locations;
    determining, by the computer, a background portion of the first image which excludes the foreground portion;
    applying, by the computer, a steerable filter or a pre-processing method to the background portion of the first image to create a non-catheter structures mask which excludes ridge-like structures in the background portion of the first image;
    generating, by the computer, a dictionary based on catheter object locations in the first image, wherein sparse coding is used to represent the non-catheter structures mask as a plurality of basis vectors in the dictionary;
    identifying, by the computer, one or more catheter object landmark candidates in the sequence of images;
    generating, by the computer, a plurality of tracking hypothesis for the catheter object landmark candidates;
    generating, by the computer, a voting score for the catheter object landmark candidates based on a voting contribution of each of a plurality of image patches used to localize the catheter object locations in the first image; and
    selecting, by the computer, a first tracking hypothesis from the plurality of tracking hypothesis based on the dictionary and the voting score.

2. The method of claim 1, wherein the selecting the first tracking hypothesis from the plurality of tracking hypothesis based on the dictionary comprises:
    determining, by the computer, a confidence score for each of tracking hypothesis included in the plurality of tracking hypothesis; and
    selecting, by the computer, a respective tracking hypothesis with the highest confidence score as the first tracking hypothesis.

3. The method of claim 1, further comprising:
    applying, by the computer, a learning algorithm to compute labels for each image in the sequence of images following the first image;
    selecting, by the computer, a plurality of images based on the computed labels; and
    updating, by the computer, the dictionary based on selected images.

4. The method of claim 3, wherein the learning algorithm is a semi-supervised learning algorithm.

5. The method of claim 1, wherein the identifying the one or more object landmark candidates in the sequence of images comprises:
    identifying, by the computer, a first set of candidate samples included in the sequence of images;
    determining, by the computer, a first stage probability score for each candidate samples in the first set;
    identifying, by the computer, a second set of candidate samples from the first set based on the first stage probability scores;
    determining, by the computer, a second stage probability score for each of the candidate samples in the second set; and
    identifying, by the computer, the catheter object landmark candidates from the second set based on the second stage probability scores.

6. The method of claim 1, wherein the identifying, by the computer, the one or more catheter object landmark candidates in the sequence of images comprises:
    identifying, by the computer, a first object landmark candidate corresponding to a first object type using one or more first classifiers trained for the first object type; and
    identifying, by the computer, a second object landmark candidate corresponding to a second object type using one or more second classifiers trained for the second object type.

7. The method of claim 6, wherein the first object type corresponds to a catheter tip and the second object type corresponds to a catheter electrode.

8. The method of claim 1, wherein the generating of the plurality of tracking hypothesis for the catheter object landmark candidates comprises:
    determining, by the computer, a set of catheter object landmarks in a previous image;
    calculating, by the computer, a plurality of translation vectors, each translation vector corresponding to a translation between one of the catheter object landmark candidates and an catheter object landmark included in the set of catheter object landmarks;
    generating, by the computer, a plurality of seed hypothesis by applying each of the translation vectors to the set of object landmarks in the previous image; and
    applying, by the computer, a geometric transformation to each seed hypothesis to generate the plurality of tracking hypothesis.

9. The method of claim 1, wherein each catheter object corresponds to at least one of a catheter tip or catheter electrode.

10. The method of claim 1, wherein the sequence of images comprises a plurality of fluoroscopic images.

11. An article of manufacture for tracking one or more catheter objects in a sequence of images, the article of manufacture comprising a computer-readable, non-transitory medium holding computer-executable instructions for performing the method comprising:
    determining a foreground portion of the first image comprising portions of the first image corresponding to one or more catheter electrode locations;
    determining a background portion of the first image which excludes the foreground portion;
    applying a steerable filter or a pre-processing method to the background portion of the first image to create a non-catheter structures mask which excludes ridge-like structures in the background portion of the first image;

generating a dictionary based on catheter object locations in the first image, wherein sparse coding is used to represent the non-catheter structures mask as a plurality of basis vectors in the dictionary;

identifying one or more catheter object landmark candidates in the sequence of images;

generating a plurality of tracking hypothesis for the catheter object landmark candidates;

generating a voting score for the catheter object landmark candidates based on a voting contribution of each of a plurality of image patches used to localize the catheter object locations in the first image; and selecting a first tracking hypothesis from the plurality of tracking hypothesis based on the dictionary and the voting score.

12. The article of manufacture claim 11, wherein the selecting the first tracking hypothesis from the plurality of tracking hypothesis based on the dictionary comprises:

determining a confidence score for each of tracking hypothesis included in the plurality of tracking hypothesis; and selecting the tracking hypothesis with the highest confidence score as the first tracking hypothesis.

13. The article of manufacture of claim 11, wherein the identifying the one or more catheter object landmark candidates in the sequence of images comprises:

identifying a first set of candidate samples included in the sequence of images;

determining a first stage probability score for each candidate samples in the first set;

identifying a second set of candidate samples from the first set based on the first stage probability scores;

determining a second stage probability score for each of the candidate samples in the second set; and identifying the object landmark candidates from the second set based on the second stage probability scores.

14. The article of manufacture of claim 11, wherein the generating of the plurality of tracking hypothesis for the catheter object landmark candidates comprises:

determining a set of catheter object landmarks in a previous image;

calculating a plurality of translation vectors, each translation vector corresponding to a translation between one of the catheter object landmark candidates and an catheter object landmark included in the set of catheter object landmarks;

generating a plurality of seed hypothesis by applying each of the translation vectors to the set of catheter object landmarks in the previous image; and applying a geometric transformation to each seed hypothesis to generate the plurality of tracking hypothesis.

15. A system for tracking one or more catheter objects in a sequence of images, the system comprising:

a receiver module operably coupled to an imaging device and configured to receive the sequence of images from the imaging device; and one or more first processors configured to:

determine a foreground portion of the first image comprising portions of the first image corresponding to one or more catheter electrode locations;

determine a background portion of the first image which excludes the foreground portion;

apply a steerable filter or a pre-processing method to the background portion of the first image to create a non-catheter structures mask which excludes ridge-like structures in the background portion of the first image;

generate a dictionary based on object locations in the first image, wherein sparse coding is used to represent non-catheter structures mask as a plurality of basis vectors in the dictionary, identify one or more catheter object landmark candidates in the sequence of images; and one or more second processors configured to:

generate a plurality of tracking hypothesis for the catheter object landmark candidates, generate a voting score for the catheter object landmark candidates based on a voting contribution of a plurality of image patches used to localize the catheter object locations in the first image, and select a first tracking hypothesis from the plurality of tracking hypothesis based on the dictionary and the voting score.

16. The system of claim 15, wherein the one or more first processors comprise one or more central processing units and the one or more second processors comprise one or more graphical processing units.

17. The system of claim 16, wherein the system further comprises:

a transfer module for transferring object landmark candidates corresponding to the first image to the central processing units for object tracking while the graphical processing units identity object landmark candidates in a second image.

18. A method of updating a dictionary to represent change in appearance of a catheter target object, the method comprising:

generating, by a computer, a non-catheter structures mask identifying structures unrelated to the target catheter object in an initial image frame;

generating, by the computer, the dictionary based on an initial appearance of the target object in the initial image frame, wherein sparse coding is used to represent non-catheter structures mask as a plurality of basis vectors in the dictionary;

receiving, by the computer, a plurality of subsequent image frames indicating a change in the initial appearance of the target catheter object;

applying, by the computer, a learning algorithm to compute labels for each of the subsequent image frames;

generating, by the computer, a voting score for each of the subsequent image frames based on a voting contribution of a plurality of image patches used to localize the catheter target object in the initial image frame, wherein the images are analyzed on a patch-by-patch basis;

selecting, by the computer, a subset of the subsequent image frames based on the computed labels and the voting score;

updating, by the computer, the dictionary based on the subset of the subsequent image frames.

19. The method of claim 18, further comprising:

receiving, by the computer, one or more additional image frames; and applying, by the computer, the updated dictionary to track the catheter target object in the additional image frames.

* * * * *